United States Patent [19]

Tsuru et al.

[11] 4,238,298
[45] Dec. 9, 1980

[54] CORROSION RATE MEASURING METHOD AND APPARATUS

[75] Inventors: Tohru Tsuru, Yokohama; Shiro Haruyama, Tokyo, both of Japan

[73] Assignee: Shiro Haruyama, Tokyo, Japan

[21] Appl. No.: 39,662

[22] Filed: May 16, 1979

[30] Foreign Application Priority Data

Oct. 2, 1978 [JP] Japan ................................ 53/120401

[51] Int. Cl.$^3$ ...................... G01N 27/02; G01N 27/06
[52] U.S. Cl. ................................. 204/1 T; 204/195 C; 324/57 R; 324/71 R
[58] Field of Search ............ 204/1 C, 195 C; 324/29, 324/57 R, 62, 65 R, 65 CR, 71 R, 425, 444

[56] References Cited

U.S. PATENT DOCUMENTS

| | | | |
|---|---|---|---|
| 3,331,021 | 7/1967 | Marsh et al. | 324/71 R |
| 4,095,176 | 6/1978 | Maes et al. | 324/65 CR |

OTHER PUBLICATIONS

S. Sathyanarayama, "A New Electrochemical Method for Instantaneous Corrosion Rate Determination,"*Electroanal. Interfacial Electrochem.*, vol. 50, pp. 441-416 (1974).

M. Prazak "The Polarization Resistance Method for Corrosion Testing," *Werkstoffe und Korrosion*, vol. 25, pp. 104-112 (1974).

P. J. Moreland et al., "Technique & Instrumentation for Polarization Resistance Measurements", *British Corrosion J.*, vol. 12, pp. 72-79 (1977).

*Primary Examiner*—Aaron Weisstuch
*Attorney, Agent, or Firm*—William J. Daniel

[57] ABSTRACT

Sample plates of the material to be evaluated for corrosion resistance are arranged on electrodes immersed in a medium substantially corresponding to the actual environment of such material during use, small alternating current voltages of differing frequency are applied between the plates so as to determine from the difference between the peak voltages of the differing frequencies as converted from the currents flowing between both plates, the alternating current impedance of the corrosion reaction, which gives an indication of the corrosion rate of the material in the medium being tested.

11 Claims, 6 Drawing Figures

CORROSION RATE MEASURING METHOD AND APPARATUS

BACKGROUND OF THE INVENTION

1. Field of the Invention

The present invention relates to a method and apparatus for experimentally determining the corrosion rate of a test plate of a given metal by applying alternating current voltages of different frequency between a pair of such plates and obtaining an indication of the corrosion resistance of the metal from the different effects of the corrosion reaction upon the resultant currents between said pair of plates.

2. Description of the Prior Art

It is very important in designing many kinds of apparatus and equipment, as regards selection of materials of construction, projecting needed maintenance for such apparatus and equipment, and preventing accidents in their operation, to know in advance with reasonable certainty the corrosion rate of a given metal when subjected to given environments. Some methods of measuring corrosion rates have been already suggested. Among these are included, for example, a corrosion weight loss method wherein the variation of the weight of a sample metal before and after being subjected to corrosion for a given time is measured, a Tafel external polarization method wherein an electric current is made to flow through a sample, its electrode potential is measured, and the linear relationship between the potential and the logarithm of the current (Tafel relation) can be used to determine the corrosion rate, a polarization resistance method wherein a small current is made to flow through a sample and the linear relationship between the potential and current is utilized, a rectangular wave polarization method wherein a small current pulse is repeatedly generated and the corrosion rate is calculated from the relation of the potential to the current, and an electric resistance method wherein the sample is made in the form of ribbon or wire, and the reduction of the cross-section due to corrosion is measured as an electric resistance variation. However, these methods have various defects. In the corrosion weight loss method, only the average corrosion rate over the period between weight measurements is given, and accurate measurement is difficult where the corrosion rate varies with the lapse of time or a significant change in weight is not obtained within a short time. In the Tafel external polarization method, the current required to satisfy the Tafel relation is so large that the errosion of the surface condition of the sample and corrosion environment will be disturbed by the electrolysis, the Tafel relation is not easy to obtain, and the determined corrosion rate will vary by a factor of at least 100 from the actual rate in most cases. In the polarization resistance and rectangular wave polarization methods, reference electrodes other than the sample plates are required and are difficult to set and maintain and results are subject to large error for corroding environments (such as, for example, in industrial water) which are high in solution resistance. In the electric resistance method, there is a danger of exaggerating the extent of localized corrosion of the sample.

SUMMARY OF THE INVENTION

The object of the present invention is to provide a method and apparatus wherein, by means of an alternating current impedance method, the corrosion rate of a metal in various environments can be continuously and automatically measured without substantially influencing the corrosion reaction.

The method of measuring the corrosion rates of metals according to the present invention is characterized in that a pair of plates made of the metal to be tested are immersed in a given spaced relation in the liquid medium substantially corresponding to the environment to which the metal is to be subjected during use, and small alternating current voltages of significantly different frequencies are simultaneously applied between the plates and the alternating current impedance of the corrosion reaction is determined from the current flowing between such plates.

A preferred embodiment of an apparatus for measuring corrosion rates according to the present invention comprises a measuring tank containing the liquid medium corresponding to the environment to be tested and a pair of plates of the metal to be evaluated at least partially immersed therein in spaced relation, a mixer-buffer connected to each of a high frequency sinusoidal wave oscillator and low frequency sinusoidal wave oscillator to provide a small alternating current voltage output signal combining the output of both sinusoidal wave oscillators, the mixer output being applied to one of a pair of test plates, a current-to-voltage converter is connected to the other plate to amplify the currents flowing through the measuring tank and convert the same to voltages, the output of the converter is delivered in parallel to a high pass filter and associated peak hold and low pass filter and associated peak hold, and the outputs of the peak hold are connected to an analyzing circuit performing the mathematical manipulations of the separate high and low frequency voltages which provides an indication of the rate at which corrosion reaction is taking place.

DETAILED DESCRIPTION OF PREFERRED EMBODIMENT

A preferred embodiment of the present invention shall be described in detail as follows. The principle of operation of the present corrosion rate measuring method is based on measurement of alternating current impedances. If an A.C. current is passed between two plates of a metal arranged as opposed electrodes in a corrosion medium, the impedance for a high frequency current will be equal to an ohmic resistance (called the solution resistance) Rs of the medium between the two electrodes, while the impedance for a low frequency current will be equal to the sum of the solution resistance Rs and corrosion reaction resistance Rc, and the corrosion reaction resistance Rc will be inversely proportional to the corrosion rate $i_{corr}$ of the metal in the medium. Thus, if the impedances Rs and Rs+Rc at high and low frequencies are measured, the difference between them is found and the reciprocal of that difference is calculated, the resultant value corresponds to the corrosion rate $i_{corr}$.

Figure 1:
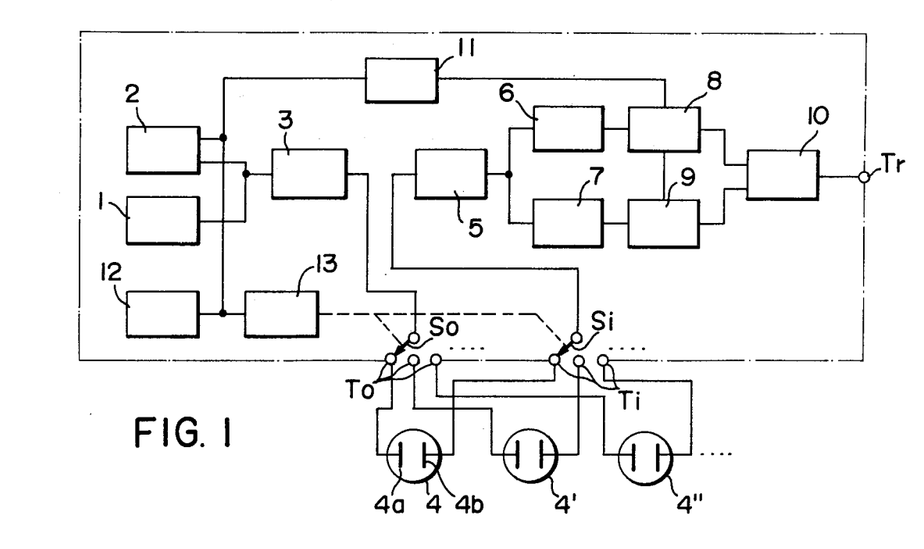
FIG. 1 is a block diagram showing a preferred embodiment of an apparatus according to the present invention.

A preferred embodiment of a circuit representing schematically an apparatus according to the invention (hereinafter referred to as a corrosion monitoring unit) is shown in FIG. 1. In the drawing, the "body" of the monitoring unit (which includes all electrical components) is enclosed within the dot-dash chain line, the actual test tanks being external to that body and connected to it via terminals.

In FIG. 1, 1 is a sinusoidal wave oscillator emitting a high frequency voltage (at least 1 KHz) and 2 is a sinusoidal wave oscillator emitting a low frequency voltage (below 1 KHz), the difference between the two frequencies being significant. The respective output voltages of the oscillators 1 and 2 are mixed with each other in a mixer-buffer 3, and the output of the mixer-buffer 3 is delivered to the output terminal To of the monitor body as small alternating current voltages of a fixed amplitude with a low output impedance. Two specimen plates 4a and 4b made of the metal to be tested are arranged as spaced electrodes in the test tank 4, one of the plates being connected to the "output" terminal To of the monitoring unit and the other to the input terminal Ti of the unit. The "input" terminal Ti is connected to a current-to-voltage converter 5 so that the alternating current flowing within the corrosion medium in the tank between the electrodes is converted and amplified to give an output voltage. The output voltage from converter 5 passes in parallel to a low pass filter 6 and a high pass filter 7 which separate the output of the converter 5 into signals of low frequency and high frequency, respectively, with noise and signal components of other frequencies removed, and then to peak holders 8 and 9, one for each filter, for detecting and holding the absolute value of the peak amplitudes received thereby after being triggered. The cut-off frequency of the low pass filter is below the high frequency level while the cut-off frequency of the high pass filter is above the low frequency level. The peak value of the amplitude of each signal passing through the filter 6 or 7 and the associated peak hold will thus appear at the output of each peak holder.

The magnitude of the alternating current voltage applied to the test electrodes in the test tank is always fixed; therefore, the variations in output voltages from the peak holds 8 and 9 are proportional to the impedances at the low frequency and high frequency, respectively. 10 is an analyzing circuit wherein the necessary mathematic operations, including subtraction and inversion according to the principle of the monitor are carried out electrically to produce at the terminal Tr an output corresponding to the corrosion rate.

The concept of this invention is ideally suited for analyzing the corrosion rate of a plurality of test samples in an associated environment medium at the same time, and the preferred embodiment depicted in FIG. 1 is arranged to accomplish this objective. Thus, the monitoring unit body includes a plurality of "output" terminals To and "input" terminals Ti, respectively, with corresponding pairs of these output and input terminals connected to the test plates in additional test tanks, 4' and 4", for example, up to the number of available terminals. An "output" switch So is effective to switch between the plural "output" terminals; while an "input" switch Si is likewise effective to switch between the plural "input" terminals to enable selected test tank and electrode plates to be connected to the monitoring unit. The switches So and Si are preferably ganged together by means of a linkage or equivalent coupling suggested in dotted lines so as to move in synchronism between corresponding pairs of the terminals and the selection of the switches can be controlled by means of a switching unit 12 which is regulated by means of an automatic switching control unit 13. In such an embodiment capable of simultaneous multiple test operations, the respective peak holds must be activated in synchronism with the regulation of the switching unit so as to correlate the output of the switch holds, and thus the ultimate output of the monitor at terminal Tr with the particular test samples being evaluated, and to this end, a timing trigger 11 is connected to both of the peak holders 8 and 9 and to the switching control unit 13 at the same time so that their functions are performed in synchronism. The timing trigger can receive timing pulses from the low frequency oscillator 2 and deliver a triggering signal after an appropriate interval.

The switching control unit can function to advance the ganged switches in a continuous cycle or it could be programmed to select among the pairs of switches in any desired sequence and, in either case, the switching control could desirably include a visual display (not separately illustrated) identifying the particular test sample being evaluated at a given instant.

According to the monitoring unit of the present invention, the corrosion rate can be measured continuously and automatically within a short time (actual time) without disturbing the sample, the corrosion environment or the course of the corrosion reaction. Further, only two samples of the test material need be prepared for the measurement to be performed In principle, the influence of the solution resistance will be eliminated and a measurement low in error will be possible. With the present monitoring unit, not only can the corrosion resistance of a metal be evaluated by measuring the corrosion rate on a laboratory scale, so that the optimum material can be selected in initially designing a given apparatus and the probable life of the material projected, but the corrosion rate in the actual apparatus can be monitored, and if desirable, a corrosion inhibitor can be added in controlled amounts as needed for optimum inhibition, using for example an automatic feeding system regulated in response to the output of the present monitoring unit.

Several examples will now be described in the following to illustrate the performance of the present monitoring unit for some of the purposes for which it can be used.

Figure 2:
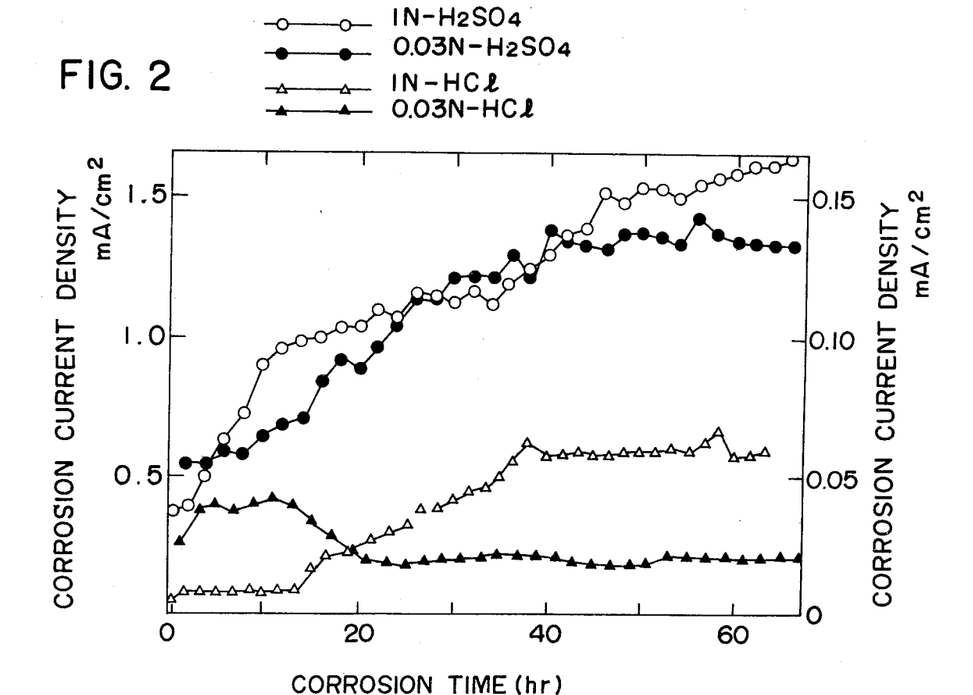
FIG. 2 is a graph plotting the relationship of the corrosion rate of iron in solutions of two acids each at two different concentrations with the time of exposure to the solution.

The variations in the corrosion rates of iron in solutions of 1 N-$H_2SO_4$, 1 N-HCl, 0.03 N-$H_2SO_4$ and 0.03 N-HCl with the lapse of times are plotted in FIG. 2. The ordinate represents the corrosion rates as expressed in current densities. From the graph, it is found that, in all cases and particularly with sulfuric acid, the corrosion rate varies significantly with time, which illustrates the fallacy in the conventional corrosion weight loss method, where only the average corrosion rate over the entire period of the measurement can be determined.

As is evident from FIG. 2, the present monitoring unit can be used not only in the selection of materials for various corrosion environments on a laboratory scale but also in a protective system wherein a fixed limit corrosion rate is set in the actual apparatus so that an alarm may be given when that limit is exceeded, or wherein the instantaneous corrosion rate outputs are integrated to give a measurement of the overall reduction in thickness of the material due to corrosion, and when that measurement exceeds a fixed limit, an alarm may be given.

Figure 3:
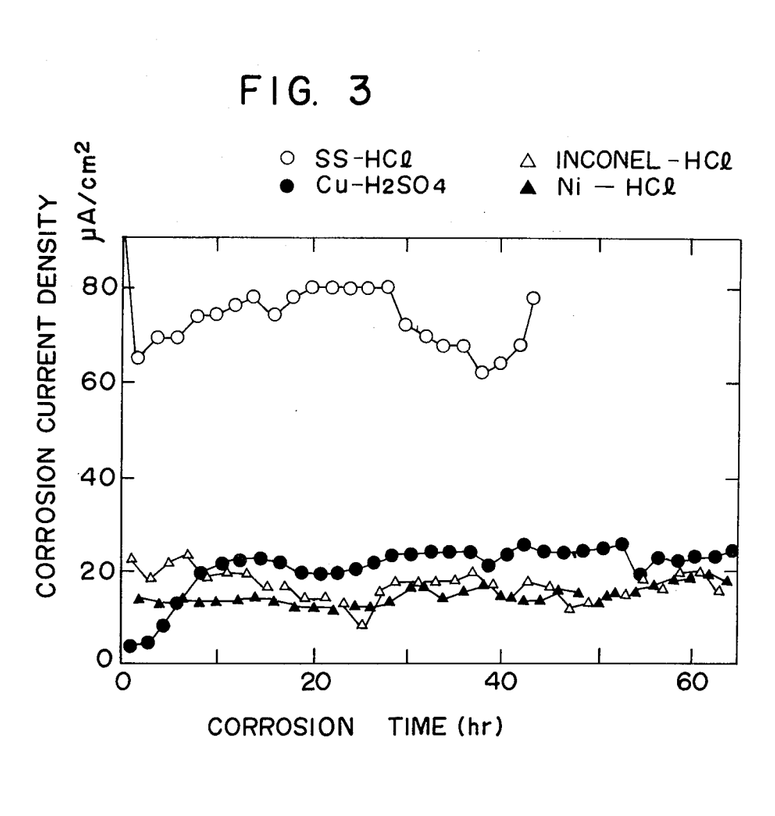
FIG. 3 is a similar graph plotting the relationships of the corrosion rates of several different metals and alloys in certain acid solutions with the time of exposure.

An example wherein the corrosion rates of Type 304-stainless steel, Inconel 600 Alloy, nickel and copper in 1N-HCl or 1N-$H_2SO_4$ were measured is plotted in FIG. 3. Obviously, the corrosion rates of other metals and alloys than these can be similarly measured.

Figure 4:
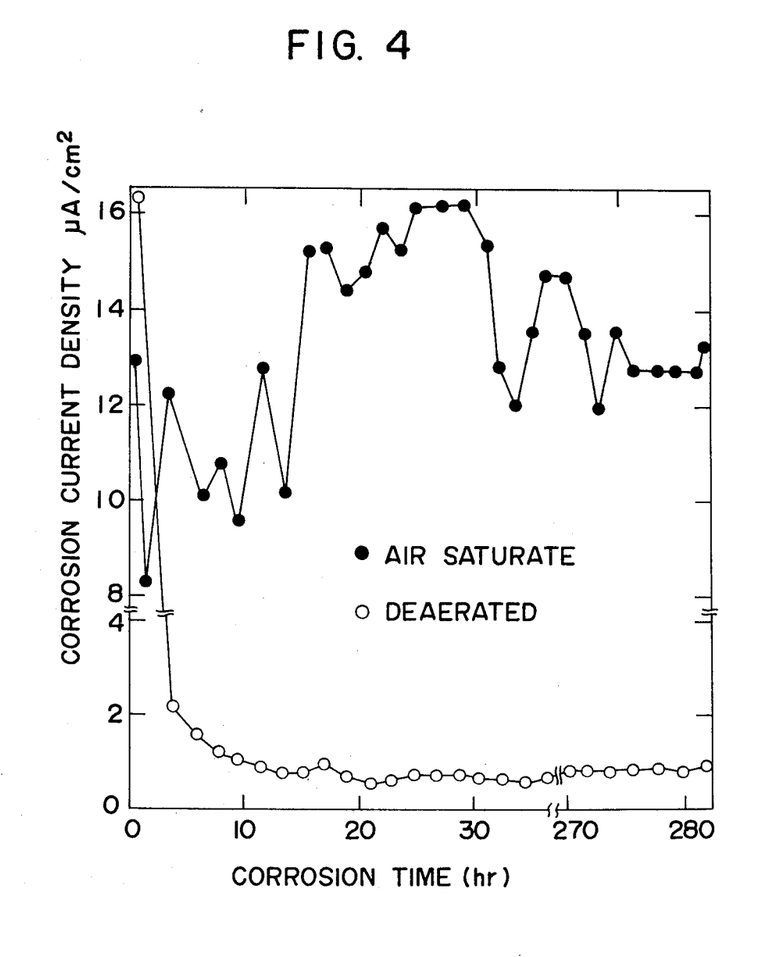
FIG. 4 is a similar graph plotting the relationship of the corrosion rate of iron in saline water of a concentration close to sea water with the time of exposure.

An example of measuring the corrosion rates in a solution containing NaCl in a concentration substantially the same as sea water is plotted in FIG. 4. In the graph, the mark ● represents a test where the sample was exposed to ambient air, while in the test represented by the mark ○ the oxygen dissolved in the solution was removed with nitrogen. It is found that, with exposure to air, the corrosion rate fluctuated rather widely apparently due to precipitation and deposition of the corrosion product on the sample surface, whereas when the oxygen was removed, the corrosion rate was very low. Thus, even if the corrosion rate varies greatly, the variation can be traced with the present monitoring unit.

Figure 5:
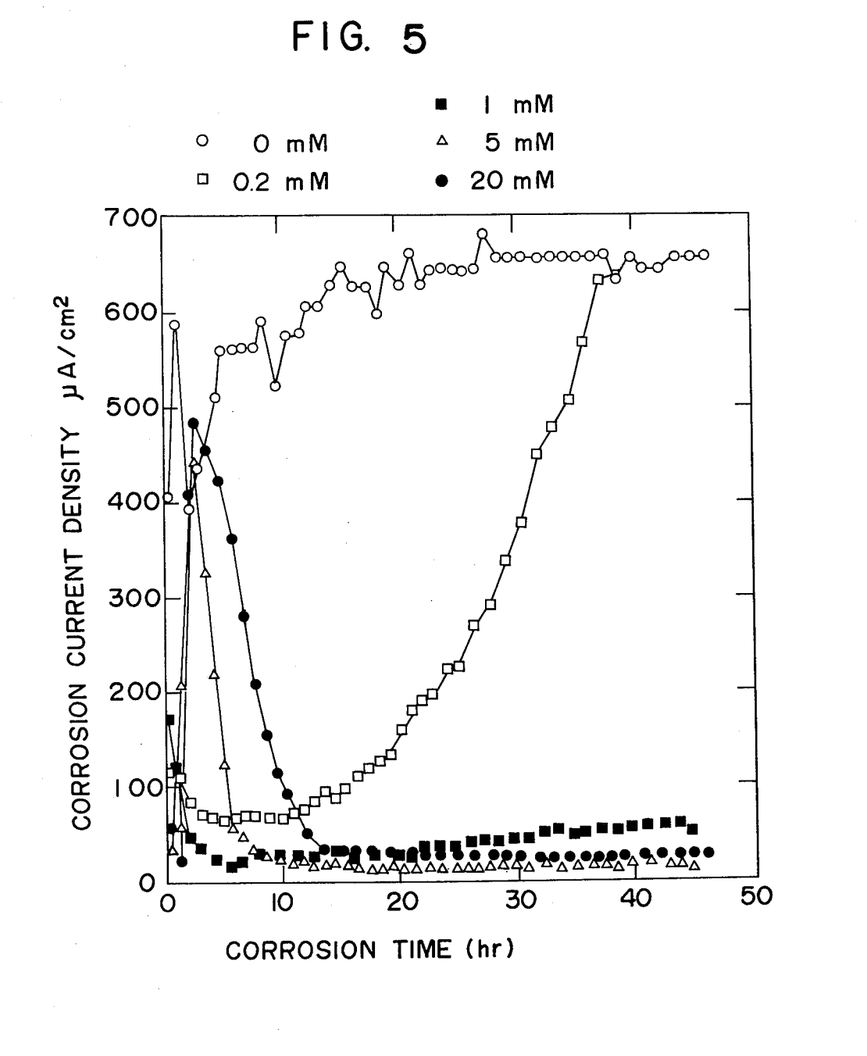
FIG. 5 is a similar graph plotting the relationship of the corrosion rate of iron in 1 N-$H_2SO_4$ solutions containing a corrosion inhibitor in various concentrations with the time of exposure.

The influence of an added corrosion inhibitor upon corrosion rate is illustrated in FIG. 5 where propargyl alcohol was added as an inhibitor to an acid solution (1N-$H_2SO_4$). The legends in the graph indicate the concentrations (in m.mol/l=mM) that were tested. It is found that, in the absence of inhibitor (identified by ○), the corrosion rate gradually increased, but with the addition of the inhibitor of a concentration of at least 1 m.mol/l., the corrosion rate was much reduced. In contrast, with the addition of 0.2 m.mol/l (identified by □), the corrosion rate was reduced initially but, with the lapse of time, the corrosion inhibiting effect gradually disappeared so that after a considerable time, corrosion occurred at substantially the same rate as when no inhibitor was added, the inhibiting effect having in effect vanished.

It is, therefore, possible not only to observe and note the corrosion inhibiting effect of an inhibitor but also to properly control the concentration and the amount in which the inhibitor is introduced, or to automatically added a proper amount of the inhibitor when the corrosion rate exceeds a fixed standard value. Further, with the invention, the corrosion rates can be continuously measured simultaneously at many different measuring points. Therefore, as compared with an intermittently working technique such as the known corrosion weight loss method, the measurement can be made almost instantaneously in response to sudden variations in the corrosion environment and can be an effective aid in preventing accidents caused by corrosion.

Figure 6:
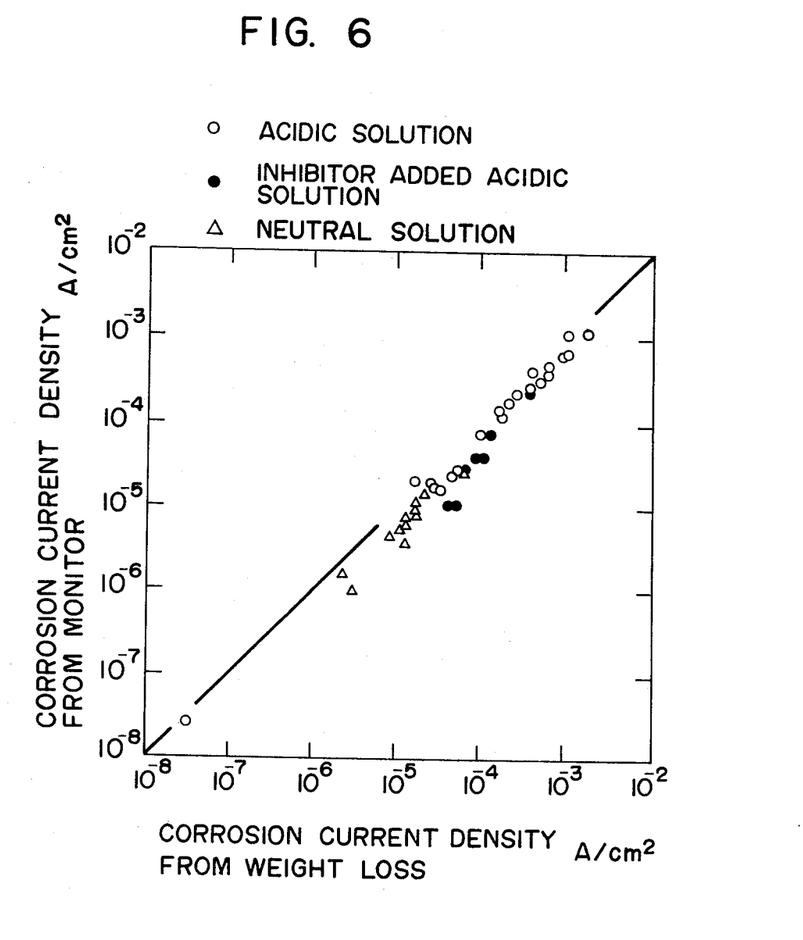
FIG. 6 is a graph comparing the results of corrosion rate measurement according to the invention with those obtained by the known corrosion weight loss method.

The measuring range and precision of the monitoring unit of the invention are shown in FIG. 6. In this graph, the ordinate represents corrosion rates in current density/unit area (A/$cm^2$) as measured with the monitor and the abscissa represents corrosion rates in current density/$cm^2$ as determined from the corrosion weight loss of the same sample. In the graph, the mark ○ represents an acid solution alone (of any concentration of HCl or $H_2SO_4$), the mark ● represents the same acid solution containing added corrosion inhibitor and the mark △ stands for a neutral solution such as tap water or sea water in combination with iron, nickel, copper and stainless steel. It appears from the graph that, in a wide corrosion rate range from $10^{-3}$ to $10^{-7}$ A/$cm^2$, the corrosion rates measured by the invention and by the corrosion weight loss are very well correlated with each other and that, with this invention, the corrosion rate can be measured with considerable precision. All of these results are for aqueous solutions; however, with the present monitoring unit, corrosion rates in a wet but non-fluid corrosion environment, such as, for example, in sea sand, mud or wet soil, could be measured in the same manner.

What is claimed is:

1. A method of measuring the corrosion rate of a given environment upon a given corrodible material which comprises arranging a given pair of test plates of said material in a given spaced relation while immersed in an environment substantially the same as said given environment, impressing two small alternating currents of differing frequency between said given pair of plates, and from the different impedances encountered by said two currents of differing voltages flowing between said given pair of plates, determining the A.C. impedance of the corrosion reaction which is a measure of the corrosion rate.

2. The method of claim 1 wherein said environment is an aqueous medium.

3. The method of claim 1 wherein said A.C. impedances are determined by converting the A.C. currents passed between said plates into voltages, isolating the high frequency and low frequency voltages, detecting the peak values of said high and low frequency voltages and determining the difference between said peak voltages which difference corresponds to the electrical resistance peculiar to the corrosion resistance and is inversely proportional to said corrosion rate.

4. The method of claim 3 including the step of calculating the reciprocal value of said peak voltage difference which is directly proportional to said corrosion rate.

5. The method of claim 3 wherein said differing voltages are applied simultaneously between said plates.

6. The method of claim 3 wherein corrosion rates are determined sequentially for a plurality of test combinations of materials and environments and including the steps of sequentially applying said currents of differing voltages selectively to the pairs of plates of said test combination and determining said peak voltage difference in timed relation to the application of said currents.

7. An apparatus for measuring the rate of the corrosion reaction of a given environment upon a given corrodible material, which apparatus employs in use a pair of test plates of said material arranged in a given spaced relation while immersed in an environment substantially the same as said given environment, said apparatus comprising means for generating high and low frequency alternating current voltages, respectively, means for applying said voltages between said pair of test plates, and means for determining the difference in impedance encountered by the A.C. currents flowing between said test plates and thereby the A.C. impedance peculiar to said corrosion reaction which is a measure of said corrosion rate.

8. The apparatus of claim 7 comprising means for converting the A.C. currents passing between said plates into voltages, means for separating the high frequency and low frequency voltages from one another, means for detecting the peak values of said high and low frequency voltages, and means for determining the difference between said peak voltages which difference corresponds to the electrical resistance peculiar to the corrosion resistance and is inversely proportional to said corrosion rate.

9. The apparatus of claim 8 including means for calculating the reciprocal value of said peak voltage difference which value is directly proportional to said corrosion rate.

10. The apparatus of claim 7 wherein said generating means comprises high and low frequency sinusoidal wave oscillators, respectively, and said applying means comprises a mixer-buffer simultaneously receiving the outputs of said oscillators and applying the mixed outputs to said test plates.

11. The apparatus of claim 7 wherein said determining means comprises a calculating circuit for subtracting said peak values, inverting the resultant value and delivering said inverted value as an output.

* * * * *